United States Patent
Ribier et al.

[11] Patent Number: 5,834,013
[45] Date of Patent: Nov. 10, 1998

[54] COSMETIC OR DERMATOLOGICAL COMPOSITION IN THE FORM OF AN AQUEOUS AND STABLE DISPERSION OF CUBIC GEL PARTICLES BASED ON PHYTANETRIOL AND CONTAINING A SURFACE-ACTIVE AGENT WHICH HAS A FATTY CHAIN, AS DISPERSING AND STABILIZING AGENT

[75] Inventors: Alain Ribier; Bruno Biatry, both of Paris, France

[73] Assignee: L'Oreal, Paris, France

[21] Appl. No.: 465,234

[22] Filed: Jun. 5, 1995

[30] Foreign Application Priority Data

Jun. 8, 1994 [FR] France ................................. 94 07031

[51] Int. Cl.$^6$ ..................................................... A61K 9/127
[52] U.S. Cl. .............................. 424/450; 424/401; 514/2; 514/944
[58] Field of Search ..................... 514/2, 944; 424/450, 424/401

[56] References Cited

U.S. PATENT DOCUMENTS 5,443,840  8/1995  Morancais et al. ..................... 424/450

FOREIGN PATENT DOCUMENTS 8402076  6/1984  WIPO .
9306921  4/1993  WIPO .

*Primary Examiner*—James J. Seidleck
*Assistant Examiner*—Michael A. Williamson
*Attorney, Agent, or Firm*—Nixon & Vanderhye, P.C.

[57] ABSTRACT

Cosmetic or dermatological composition in the form of an aqueous and stable dispersion of cubic gel particles based on 3,7,11,15-tetramethyl-1,2,3-hexadecanetriol or phytanetriol and use thereof for hydrating the skin.

This composition essentially comprises:
(a) from 0.1 to 15% by weight of 3,7,11,15-tetramethyl-1,2,3-hexadecanetriol relative to the total weight of the composition, and
(b) from 0.1 to 3% by weight of a dispersing and stabilizing agent relative to the total weight of the composition, the said agent being chosen from surface-active agents that are water-soluble at room temperature, containing a saturated or unsaturated fatty chain having from 8 to 22 carbon atoms.

This composition is of excellent stability and has a very satisfactory sensory feel and a hydrating effect, and moreover allows hydrophilic and/or lipophilic active principles to be included therein without any problem of compatibility.

31 Claims, No Drawings

COSMETIC OR DERMATOLOGICAL COMPOSITION IN THE FORM OF AN AQUEOUS AND STABLE DISPERSION OF CUBIC GEL PARTICLES BASED ON PHYTANETRIOL AND CONTAINING A SURFACE-ACTIVE AGENT WHICH HAS A FATTY CHAIN, AS DISPERSING AND STABILIZING AGENT

The subject of the present invention is a cosmetic or dermatological composition for topical use, in the form of an aqueous and stable dispersion of cubic gel particles based on 3,7,11,15-tetramethyl-1,2,3-hexadecanetriol or phytanetriol and containing a water-soluble surface-active agent which has a fatty chain, as dispersing and stabilizing agent.

The various active principles generally present in cosmetic and dermatological compositions may be hydrophilic or lipophilic in nature and thus require vehicles that are compatible with their respective nature. When it is desired to formulate simultaneously hydrophilic and lipophilic active principles, it is common practice to prepare so-called two-phase compositions, that is to say compositions comprising an aqueous phase and a lipid phase. The most classic examples of these type of compositions are, of course, emulsions, either of water-in-oil or oil-in-water type. However, it is well known that during its application, the emulsion "breaks", thus suddenly releasing the active principles which it contained. These principles are then absorbed by the skin, their rate of penetration varying considerably depending on their nature. Thus, emulsions appear to be a fairly unsatisfactory vehicle when the simultaneous presence of active principles of different nature is desired in at least one determined layer of the skin, in particular for the purpose of obtaining a synergy effect between the various active principles.

U.S. Pat. No. 5,151,272 has described controlled-release compositions and in particular gels, especially transdermal compositions, of active principles. Such compositions are in the form of a liquid crystal phase, especially a cubic phase, consisting of a mixture of water and monoolein and optionally combined with phosphatidylcholine.

The cubic phases are generally in the form of viscous transparent gels that are isotropic in polarized light. They are organized in a bipolar manner into distinct hydrophilic and lipophilic domains, in close contact and forming a thermodynamically stable three-dimensional network. Such an organization has been described in particular in "La Recherche, vol. 23, pp. 306–315, March 1992" and in "Lipid Technology, vol. 2, No. 2, pp. 42–45, April 1990". Depending on the arrangement of the hydrophilic and lipophilic domains, the cubic phase is said to be of normal or reverse type. The term "cubic gel" used in the present invention obviously groups together the various types of cubic phases.

The production of transparent aqueous gels from phytanetriol and water has also been described in JP 92-69316.

However, these compositions in gel form having a cubic liquid crystal phase structure are of high viscosity and feel sticky, coarse and tacky, and thus have unsatisfactory sensory properties.

WO 93/06921 has described particle dispersions consisting of a non-lamellar inner phase in the form of a cubic or hexagonal liquid crystal phase or of an L3 liquid crystal phase and a liquid crystal or L3, lamellar outer phase. Such a structure is obtained by association of monoolein and water or monoolein, phosphatidylcholine and water, in order to form a homogeneous liquid crystal phase which is then broken, in the presence of a solvent and generally of a surface-active agent in particular such as amphiphilic block polymers, for instance poloxamers, also referred to as Pluronic, in order to form a particle dispersion.

However, these dispersions have a major drawback, namely, their lack of stability. Indeed, the appearance of crystals has been observed when the dispersion was stored at low temperature (+4° C.). This phenomenon materializes the loss in structure, cubic and continuous, of the particles, and thus the loss of the sequestration/release properties expected of these dispersions.

It has now been observed, surprisingly and unexpectedly, that it was possible to obtain stable cosmetic or dermatological compositions containing cubic gel particles in dispersed form, which have both hydrophilic and lipophilic domains enabling hydrophilic and lipophilic active principles to be included therein, these particles having a reduced and controllable lattice which makes it possible to modulate the availability of the active principles sequestered. These compositions thus constitute an ideal support for active principles of opposite and incompatible polarity or of complementary or even synergistic activity. These compositions not only have excellent stability but also a very satisfactory sensory feel, and are obtained by dispersing cubic gel particles based on phytanetriol in an aqueous medium in the presence of at least one water-soluble surface-active agent which has a fatty chain.

The subject of the present invention is thus a cosmetic or dermatological composition for topical use, in the form of an aqueous and stable dispersion of cubic gel particles based on phytanetriol, comprising:

(a) from 0.1 to 15% by weight of 3,7,11,15-tetramethyl-1,2,3-hexadecanetriol or phytanetriol relative to the total weight of the composition, and (b) from 0.1 to 3% by weight of a dispersing and stabilizing agent relative to the total weight of the composition, the said agent being selected from surface-active agents that are water-soluble at room temperature, containing a linear or branched, saturated or unsaturated fatty chain having from 8 to 22 carbon atoms.

According to a preferred embodiment of the aqueous compositions according to the invention, the proportion of phytanetriol is between 0.5 and 10% by weight relative to the total weight of the composition.

The weight ratio between the phytanetriol and the said dispersing and stabilizing agent as defined above is preferably between 1 and 200, and in a particularly preferred manner is between 2 and 50.

Phytanetriol is a known compound which is marketed in particular under the name "Phytantriol-63926"® by the company Roche.

The dispersing and stabilizing agent as defined above is preferably selected from:

(1) polyol alkyl or alkenyl ethers or esters, (2) N-acylated amino acids and derivatives thereof and N-acylated peptides with an alkyl or alkenyl radical, and salts thereof, (3) alkyl or alkenyl ether or ester sulphates, and derivatives and salts thereof, (4) polyoxyethylenated alkyl or alkenyl fatty ethers or esters, (5) polyoxyethylenated alkyl or alkenyl carboxylic acids and salts thereof, (6) N-alkyl or N-alkenyl betaines, (7) alkyltrimethylammonium or alkenyltrimethylammonium and salts thereof, and mixtures of the above dispersing and stabilizing agents.

In the compounds listed above, the alkyl and alkenyl radicals have from 8 to 22 carbon atoms and may be in the form of mixtures.

1—Polyol alkyl or alkenyl ethers or esters

Among these, there may in particular be mentioned sorbitan alkyl or alkenyl esters polyoxyethylenated with at least 20 units of ethylene oxide, such as sorbitan palmitate 20 EO or Polysorbate 40 marketed under the name "Montanox 40 DF"® by the company Seppic, and sorbitan laurate 20 EO or Polysorbate 20 marketed under the name "Tween 20"® by the company ICI.

In this group, there may also be mentioned polyglyceryl alkyl or alkenyl esters containing at least 10 units derived from glycerol, which may or may not be oxyethylenated, such as polyglyceryl-10 laurate marketed under the name "Decaglyn 1-L"® by the company Nikko Chemicals.

There may also be mentioned the alkyl or alkenyl ethers or esters of mono- or polysaccharides such as those derived from glucose, fructose, galactose, maltose or lactose and especially the monoesters in positions -1 and -6 of D-fructose, decylglucose or decylpolyglucose.

2—N-Acylated amino acids and derivatives thereof and N-acylated peptides with an alkyl or alkenyl radical and salts thereof.

Among these, those for which the alkyl or alkenyl radical has at least 12 carbon atoms are preferably used.

According to the invention, the term amino acids refers to α, β or γ-amino acids. As N-acylated amino acid salts, there may for example be mentioned those of N-acylated glutamate such as monosodium cocoyl glutamate, monosodium lauroyl glutamate, disodium $C_{14}$–$C_{20}$ alkoyl glutamate (the $C_{14}$–$C_{20}$ alkoyl radical being derived from hydrogenated tallow), respectively marketed under the names "Acylglutamate CS-11"®, "Acylglutamate LS-11"® and "Acylglutamate HS-21"® by the company Ajinomoto.

There may also be mentioned N-acylated lysines such as lauroyllysine marketed under the name "Amihope LL"® by the company Ajinomoto. There may also be mentioned N-acylated aminopropionate.

The N-acylated amino acid derivatives and salts thereof are preferably N-acylated sarcosinates, such as sodium lauroyl sarcosinate marketed under the name "Oramix L30"® by the company Seppic, sodium myristoyl sarcosinate and sodium palmitoyl sarcosinate respectively marketed under the names "Nikkol Sarcosinate MN"® and "Nikkol Sarcosinate PN"®, by the company Nikko Chemicals.

Among the N-acylated peptides, there may be mentioned those derived from all or part of collagen or keratin, such as sodium lauroyl collagen and palmitoyl keratin marketed under the names "Proteol B 30"® and "Lipacide PK"® by the company Seppic.

3—Alkyl or alkenyl ether or ester sulphates, and the derivatives and salts thereof Among these, those for which the alkyl or alkenyl radical has at least 12 carbon atoms are preferably used.

Among the alkyl or alkenyl ether sulphates, the alkyl ether sulphate salts, and in particular sodium lauryl ether sulphate, are preferably used.

Among the alkyl or alkenyl ester sulphates, there may for example be mentioned the esters of isethionic acid and the salts thereof, and in particular sodium cocoyl isethionate marketed under the name "Geropon AC 78"® by the company Rhône Poulenc.

4—Polyoxyethylenated alkyl or alkenyl fatty ethers or esters

Among these, those for which the alkyl or alkenyl radical has at least 12 carbon atoms are preferably used. Those particularly preferred have at least 20 units of ethylene oxide, for example such as PEG-20 stearate, laureth-23, oleth-20 and PEG-25 phytosterol.

5—Polyoxyethylenated alkyl or alkenyl carboxylic acids and salts thereof

Among these, those containing at least 10 ethylene oxide units are preferably used, for example such as laureth-10 carboxylic acid and oleth-10 carboxylic acid.

6—N-alkyl or N-alkenylbetaines

Among these, those for which the alkyl or alkenyl radical has at least 12 carbon atoms are preferably used, for example such as laurylamidopropyl betaine and oleylamidopropyl betaine.

7—Alkyltrimethylammonium or alkenyltrimethylammonium and salts thereof

Among these, those for which the alkyl or alkenyl radical has at least 12 carbon atoms are preferably used. The bromides and chlorides, such as cocoyltrimethyl-ammonium chloride and cetyltrimethylammonium bromide, are preferably used as salts.

The cosmetic or dermatological compositions in dispersion form according to the invention have a pH generally between 5 and 8 and preferably between 6 and 7.

The compositions according to the invention are stable and may be stored for 2 months at a temperature between 4° and 45° C., without displaying any variation in macroscopic or microscopic appearance, or in colour or odour.

According to a specific embodiment of the compositions according to the invention, the cubic gel particles additionally comprise from 0.0005% to 5% by weight and preferably from 0.001% to 2% by weight of a water-insoluble ionic amphiphilic lipid.

Among these, there may in particular be mentioned:

(i) phospholipids such as natural phospholipids, for instance soya or egg lecithin, chemically or enzymatically modified phospholipids, for instance hydrogenated lecithin or phosphatidic acid sodium salt, and synthetic phospholipids such as dipalmitoylphosphatidyl-choline, (ii) fatty alcohol phosphoric acid phosphonic esters such as monocetyl phosphate and the sodium and potassium salts thereof, marketed under the name "Monafax 160"® by the company Mona, and dimyristyl phosphate and the sodium and potassium salts thereof, marketed under the name "Mexoryl SY"® by the company Chimex, (iii) N-acylated derivatives of glutamic acid, such as monosodium stearoyl glutamate marketed under the name "Acylglutamate HS 11"® by the company Ajinomoto and the monosodium cocoyl-($C_{14}$–$C_{20}$) alkoyl glutamate mixture, the $C_{14}$–$C_{20}$ alkoyl radical being derived from hydrogenated tallow, marketed under the name "Acylglutamate GS 11"® by the company Ajinomoto, (iv) sodium cetyl sulphate marketed under the name "Nikkol SCS"® by the company Nikko Chemicals, (v) sodium cocoyl monoglyceride sulphate marketed under the name "Nikkol SGC 80 N"® by the company Nikko Chemicals, and (vi) quaternary ammonium derivatives such as behenyltrimethylammonium chloride, dilauryldimethylammonium chloride, distearyldimethylammonium chloride and 4,5-dihydro-1-methyl-2-($C_{14}$–$C_{20}$)alkoyl-1-(2-($C_{14}$–$C_{20}$)-alkoyl-aminoethyl) imidazolium methyl sulphate, the $C_{14}$–$C_{20}$ alkoyl radicals being derived from hydrogenated tallow, marketed under the name "Rewoquat W75H"® by the company Rewo Chemische, and dialkylhydroxyethylmethylammonium methyl sulphate in which the alkyl radicals are derived from tallow, which may or may not be hydrogenated, marketed under the name "Stepanquat VP 85"® by the company Stepan and quaternium-82 marketed by the company Seppic under the name "Amonyl DM"®.

The incorporation of these water-insoluble ionic amphiphilic lipids imparts a surface charge to the cubic gel particles which causes mutual electrostatic repulsion of the particles.

The cosmetic or dermatological compositions in the form of a dispersion of cubic gel particles as defined above are obtained by breaking, using a homogenizer, a cubic gel based on phytanetriol, water and at least one water-soluble surface-active agent which has a fatty chain as defined above and possibly based on water-insoluble ionic amphiphilic lipids as defined above and/or on hydrophilic and lipophilic active principles.

The cubic gel particles may be obtained by various suitable mechanical means such as, for example, by a homogenizer of rotor-stator type with a high shear gradient, such as "Virtis", or by a high-pressure homogenizer operating between 200 and 1800 bar approximately (20 to 180 mPa).

The average size of the particles in the dispersion, as defined above, is generally approximately from 0.05 to 1 μm and preferably less than or equal to 0.5 μm. The particle size of the dispersion may moreover be modulated by the nature and concentration of the fatty-chain-containing water-soluble surface-active agent used.

It is possible to incorporate into the cubic gel particles of the dispersions as defined above, various types of active compounds. In particular, the said particles may contain a hydrophilic active principle or a lipophilic active principle.

Obviously, by virtue of the specific structure of the cubic gel particles, it is possible to incorporate into the latter both hydrophilic active principles and lipophilic active principles even if there is a certain incompatibility between these active principles.

Among the various active principles which may be incorporated, there may in particular be mentioned:

1) Antioxidants or anti-free-radical agents such as:
proteins and enzymes such as superoxide dismutase (SOD), lactoperoxydase and lactoferrin,
peptides and derivatives thereof, such as taurine and carnosine,
sequestering agents such as phytic acid and polyphosphonic derivatives,
flavonoids such as rutin and α-glycosyl rutin,
chlorophyllin,
ethoxyquine,
guanosine,
tocopherols, especially α,β- or γ-tocopherols and in particular d-α-tocopherol marketed under the name "Covitol F 1300"® by the company Henkel and tocopheryl acetate,
ascorbyl palmitate, and
β-carotene, 2) Hydrating agents or humectants such as:
hyaluronic acid and the sodium salt thereof,
β-glycerophosphate,
glycerol, and
sorbitol, 3) UV screening agents such as:
the products marketed under the names "Eusolex 232"® by the company Merck, "Parsol 1789"® and "Parsol MCX"® by the company Givaudan-Roure, "Mexoryl SX"® by the company Chimex and "Uvinul T150"® by the company BASF, 4) Keratolytic agents such as:
proteolytic enzymes such as subtilisin, trypsin, α-chymotrypsin and papain,
salicylic acid and derivatives thereof such as 5-n-dodecanoylsalicylic acid, and
retinoic acid, 5) tanning accelerators such as:
caffeine, and
tyrosine derivatives such as glucose tyrosinate and N-L-malyltyrosine disodium salt, 6) depigmenting agents such as:
kojic acid,
glycolic acid,
vitamin C and especially magnesium ascorbyl phosphate, and
arbutin and derivatives thereof, 7) natural dyes such as:
dyestuffs extracted from plants, such as chlorophyllin and β-carotene, or extracted from animals, such as cochineal carmine, and
caramel, 8) Self-tanning agents such as:
dihydroxyacetone, and
indoles, 9) lipid regulators such as:
γ-orizanol,
extract of *Centella asiatica* containing genin and asiatic acid,
caffeine, and
theophylline, 10) Anti-ageing and anti-wrinkle agents such as:
hydroxy acids such as glycolic acid,
n-octanoylsalicylic acid,
retinol and derivatives thereof such as retinyl acetate, palpitate and propionate, and
retinoids, 11) Anti-inflammatory and cicatrizing agents such as:
18-β-glycyrrhetinic acid and salts thereof, in particular such as the ammonium salt thereof,
α-bisabolol,
corticoids, and
extract of *Centella asiatica*, 12) Antibacterial and antifungal agents such as:
benzalkonium chloride,
chlorhexidine,
hexetidine, and
hexamidine, 13) insect repellents such as:
diethyl and dimethyl toluamides, 14) Deodorants such as:
hexachlorophene, and
triclosan, the product marketed under the name "Irgasan DP 300"® by the company Ciba-Geigy, 15) Anti-dandruff agents such as:
octopirox, and
pyridinethione derivatives such as those marketed under the names "Omadinel"® by the company Olin, 16) Agents for combating hair loss such as:
methyl or hexyl nicotinate, and
minoxidil, 17) Hair dyes such as:
oxidation couplers and bases,
direct dyes, and
auto-oxidizable dyes, 18) permanent-waving reducing agents such as:
thioglycolic acid,
cysteine,
cysteamine,
N-acetylcysteine,
N-acetylcysteamine, and
glyceryl thioglycolate, 19) Conditioners for skin and hair such as:
cationic polymers and cations.

The compositions in dispersion form according to the invention may thus comprise either particles containing hydrophilic active principles, or particles containing lipophilic active principles, or particles containing both hydrophilic and lipophilic active principles, for example such as hydrophilic and lipophilic UV screening agents, or a mixture of these various particles.

It is also possible to incorporate into the continuous aqueous phase of the dispersion various cosmetically or dermatologically acceptable compounds such as hydrophilic active principles, for instance conventional additives or hydrating agents.

Among these additives, there may in particular be mentioned preserving agents, fragrances, pigments ($TiO_2$), dyestuffs, fillers, gelling agents, etc.

The compositions according to the invention may also comprise, besides the dispersed cubic gel particles, liposomes optionally containing active principles.

The presence of phytanetriol in the compositions according to the invention imparts good hydrating power thereto.

Another subject of the present invention is thus the use of a composition as defined above for hydrating the skin by topical application.

A further subject of the invention is a method for hydrating the skin, comprising the application of a composition as defined above to the skin.

Examples of preparation of aqueous dispersions according to the invention for cosmetic and dermatological use will now be given by way of illustration.

EXAMPLE 1

Cosmetic composition in the form of a dispersion of cubic gel particles of phytanetriol stabilized with polysorbate 40

18.57 g of an aqueous solution containing 2% of polysorbate 40 marketed under the name "Montanox 40 DF"® by the company Seppic are added to a cubic gel obtained by mixing 1 g of phytanetriol with 0.43 g of water. After predispersing the mixture thus obtained, it is then homogenized at room temperature using a "Virtis" type homogenizer at 35,000 rev/min for 5 minutes, this stirring being repeated 4 times.

The composition in dispersion form thus obtained is homogeneous and stable. When stored between 4° C. and 45° C. for 2 months, it in fact displays neither any variation in colour, nor in odour, nor the appearance of crystals.

The average particle size, measured using a CBI 90 laser granulometer from the company Brookhaven Instruments Corporation, is about 0.48 µm.

When applied to the skin, the composition in dispersion form thus obtained spreads easily and has satisfactory sensory qualities as well as good hydrating power.

Evaluation of the hydrating effect of phytanetriol

The hydrating effect of phytanetriol was evaluated according to the method described in "Impedance methods for studying skin moisturization", J. L. Lévèque et al., Journ. Soc. Cosmet. Chem., 34, 419–428, December 1983.

According to this method, the increase in water content of the skin is correlated with an increase in the electrical conductance thereof and thus allows an indirect measurement of the hydration of the skin.

One of the following compositions is applied to the forearms of 12 individuals having so-called "dry" skins, at an amount of 2 mg/cm²:

Composition A (according to the invention):
Composition of Example 1, that is to say containing 5% by weight of phytanetriol and 1.7% by weight of polysorbate 40 relative to the total weight of the composition, Composition B (comparative):
Aqueous dispersion of cubic gel particles prepared according to the procedure described in Patent Application WO 93/06921, containing 5% of monoolein and 1.7% of an amphiphilic block polymer marketed under the name "Pluronic F127"® by the company BASF, the percentages being expressed by weight relative to the total weight of the composition, Composition C (comparative):
Aqueous solution containing 1.7% by weight of polysorbate 40 relative to the total weight of the composition.

One hour after the application, the high-frequency (10 MHz) electrical conductance is measured using a "Dermodiag" type machine according to the principle described in BF 73/10935 and BF 75/18905.

The results are expressed as a variation in hydration relative to the naked skin and are presented in the following table:

| Composition | A | B | C | Naked skin |
|---|---|---|---|---|
| Variation in hydration 1 h after application | 14 ± 7 | 6 ± 4* | 3 ± 6* | −1 ± 4* |

*Values which are not significantly different according to the statistical test entitled "Analyse des Variances" [Analysis of Variances] or ANOVA test.

It is thus seen that only composition A in the form of a dispersion of cubic gel particles of phytanetriol and polysorbate 40 has a hydrating effect on the skin, it not being possible for this effect to be obtained using compositions B and C as defined above. Insofar as no hydrating effect is observed after application of composition C, the hydrating effect observed after application of composition A does indeed result from the presence of the phytanetriol.

EXAMPLE 2

Cosmetic composition in the form of a dispersion of cubic gel particles based on phytanetriol and on a lecithin stabilized with polysorbate 40.

19 g of an aqueous solution containing 1% of polysorbate 40 are added to a cubic gel obtained by mixing 0.3 g of water and 0.7 g of a mixture in a 70/30 ratio by weight of phytanetriol and a lecithin marketed under the name "Epikuron 145 V"® by the company Lucas Meyer. The mixture is then homogenized at room temperature using a "Heidolph" type homogenizer (Diax 600) fitted with an 18 G dispersion head, at 25,000 rev/min for 15 minutes.

The composition thus obtained is homogeneous and stable.

The average size of the particles is about 0.17 µm.

EXAMPLE 3

Cosmetic composition in the form of a dispersion of cubic gel particles of phytanetriol containing 0.05% of superoxide dismutase (SOD) stabilized with polyglyceryl-10 laurate.

19 g of an aqueous solution containing 2% of polyglyceryl-10 laurate marketed under the name "Decaglyn 1-L"® by the company Nikko Chemicals are added, after equilibrating, to 1 g of cubic gel obtained by mixing, at room temperature, 0.7 g of phytanetriol and 0.3 g of an aqueous solution containing 10 mg of SOD. The mixture thus obtained is homogenized at room temperature using a "Soavi" type high-pressure homogenizer by 4 passages at 600 bar.

The composition thus obtained is homogeneous and stable. When applied to the skin, it imparts a protective effect against attack by free radicals which accelerates the ageing of the skin. This composition thus has an excellent anti-ageing effect.

The average size of the particles is about 0.14 µm.

EXAMPLE 4

Cosmetic composition in the form of an aqueous dispersion of cubic gel particles of phytanetriol containing D-α-tocopherol and superoxide dismutase (SOD) stabilized with polysorbate 40.

19 g of an aqueous solution containing 1% of polysorbate 40 are added, at room temperature, to a cubic gel obtained by mixing 0.7 g of a mixture of phytanetriol and α-tocopherol (97/3) with 0.3 g of an aqueous solution containing 10 mg of SOD. The mixture thus obtained is homogenized at room temperature using a "Heidolph" type homogenizer (Diax 600) fitted with an 18 G dispersion head, at 25,000 rev/min for 15 minutes. The composition obtained is stable and homogeneous and contains anti-free-radical agents of both hydrophilic and lipophilic type.

The average size of the particles of the composition is about 0.26 µm.

EXAMPLE 5

Cosmetic composition in the form of a dispersion of cubic gel particles of phytanetriol containing "Parsol MCX"® and "Mexoryl SX"® stabilized with polysorbate 40.

19 g of an aqueous solution containing 1% of polysorbate 40 are added to 1 g of the cubic gel obtained by mixing 7 g of a mixture in a 93/3 ratio by weight of phytanetriol and a lipophilic sunscreen marketed under the name "Parsol MCX"® by the company Givaudan-Roure with 3 g of an aqueous solution containing 0.455 g of a hydrophilic sunscreen marketed under the name "Mexoryl SX"® by the company Chimex. The mixture is homogenized at room temperature using a "Heidolph" type homogenizer (Diax 600) fitted with an 18 G dispersion head, at 25,000 rev/min for 15 minutes.

The composition thus obtained is stable and homogeneous, comprising a combination of sunscreens covering a wide radiation spectrum, and thus constitutes a good antisun product.

The average size of the particles of the cubic gel is about 0.25 µm.

EXAMPLE 6

Cosmetic composition in the form of a dispersion of cubic gel particles of phytanetriol and monocetyl phosphate containing ethoxyguine, lactoperoxidase and lactoferrin, stabilized with polysorbate 40.

92.9 g of an aqueous solution containing 1.4 g of polysorbate 40 and 0.0125 g of sodium hydroxide are added after equilibrating, at room temperature, to 7.1 g of the cubic gel obtained by mixing together the following compounds:

Phytanetriol 4.85 g
Monocetyl phosphate marketed under the name "Monofax 160"® by the company Mona 0.1 g
Ethoxyquine marketed under the name "Raluquin"® by the company Raschig 0.05 g
Aqueous solution containing 0.05 g of lactoperoxidase and 0.04 g of lactoferrin marketed by the company Bioserae 2.1 g The mixture obtained is homogenized at room temperature using a "Virtis" type homogenizer at 35,000 rev/min for 3 minutes, this stirring being repeated twice.

The composition thus obtained is homogeneous and stable and constitutes an excellent anti-ageing product.

The average size of the particles is about 0.20 µm.

We claim:

1. A cosmetic or dermatological composition for topical use, containing in an aqueous phase, a stable dispersion of cubic gel particles, wherein:

said dispersed cubic gel particles contain from 0.1 to 15% by weight of 3,7,11,15-tetramethyl-1,2,3-hexadecanetriol or phytanetriol relative to the total weight of the composition, and said aqueous phase contains an agent for dispersing and stabilizing said cubic gel particles in said aqueous phase, said agent being present from 0.1 to 3% by weight relative to the total weight of the composition and said agent being a water-soluble surface-active agent at room temperature, containing a linear or branched, saturated or unsaturated fatty chain having from 8 to 22 carbon atoms.

2. The composition according to claim 1, wherein the proportion of phytanetriol is between 0.5 and 10% by weight relative to the total weight of the composition.

3. The composition according to claim 1, wherein the weight ratio between the phytanetriol and the said dispersing and stabilizing agent is between 1 and 200.

4. The composition according to claim 3, wherein the weight ratio between the phytanetriol and the said dispersing and stabilizing agent is between 2 and 50.

5. The composition according to claim 1, wherein the said stabilizing agent is selected from the group consisting of:
 (1) polyol alkyl or alkenyl ethers or esters,
 (2) N-acylated amino acids and derivatives thereof and peptides N-acylated with an alkyl or alkenyl radical, and salts thereof,
 (3) alkyl or alkenyl ether or ester sulphates, and the derivatives and salts thereof,
 (4) polyoxyethylenated alkyl or alkenyl fatty ethers or esters,
 (5) polyoxyethylenated alkyl or alkenyl carboxylic acids and salts thereof,
 (6) N-alkyl or N-alkenyl betaines,
 (7) alkyltrimethylammonium or alkenyltrimethylammonium and salts thereof, and mixtures thereof.

6. The composition according to claim 5, wherein said polyol alkyl or alkenyl ethers or esters are selected from the group consisting of alkyl or alkenyl esters of sorbitan polyoxyethylenated with at least 20 units of ethylene oxide, polyglyceryl alkyl or alkenyl esters containing at least 10 units derived from glycerol, optionally oxyethylenated, and alkyl or alkenyl mono-or polysaccharide ethers or esters.

7. The composition according to claim 6, wherein the said polyol alkyl or alkenyl ethers or esters are selected from the group consisting of sorbitan palmitate 20 EO, sorbitan laurate 20 EO, polyglyceryl-10 laurate, and the monoesters in positions -1 and -6 of D-fructose, decylglucose or decylpolyglucose.

8. The composition according to claim 5, wherein said N-acylated amino acids and derivatives thereof and said N-acylated peptides and salts thereof are selected from the group consisting of N-acylated glutamates, N-acylated lysines, N-acylated aminopropionates, N-acylated sarcosinates, N-acylated collagen and N-acylated keratin.

9. The composition according to claim 8, wherein said N-acylated amino acids and derivatives thereof and said N-acylated peptides and salts thereof are selected from the group consisting of monosodium cocoyl glutamate, monosodium lauroyl glutamate, disodium $C_{14}$–$C_{20}$ alkoyl glutamate, the alkoyl radical being derived from hydrogenated tallow, lauroyl lysine, sodium lauroyl sarcosinate, sodium myristoyl sarcosinate, sodium palmitoyl sarcosinate, sodium lauroyl collagen and palmitoyl keratin.

10. The composition according to claim 5, wherein said alkyl or alkenyl ether or ester sulphate salts are selected from the group consisting of sodium lauryl ether sulphate and sodium cocoyl isethionate.

11. The composition according to claim 5, wherein said polyoxyethylenated alkyl or alkenyl fatty esters or ethers contain at least 20 units of ethylene oxide.

12. The composition according to claim 11, wherein said polyoxyethylenated alkyl or alkenyl fatty esters or ethers are selected from the group consisting of PEG-20 stearate, laureth-23, oleth-20 and PEG-25 phytosterol.

13. The composition according to claim 5, wherein said polyoxyethylenated alkyl or alkenyl carboxylic acids and salts thereof contain at least 10 units of ethylene oxide.

14. The composition according to claim 13, wherein said polyoxyethylenated alkyl or alkenyl carboxylic acids are selected from the group consisting of laureth-10 carboxylic acid and oleth-10 carboxylic acid.

15. The composition according to claim 5, wherein said N-alkyl or N-alkenyl betaines are selected from the group consisting of laurylamidopropyl betaine and oleylamidopropyl betaine.

16. The composition according to claim 5, wherein said alkyltrimethylammonium or alkenyltrimethylammonium salts are selected from the group consisting of cocoyltrimethylammonium chloride and cetyltrimethylammonium bromide.

17. The composition according to claim 1 wherein the said cubic gel particles further contain from 0.0005% to 5% by weight of at least one water-insoluble ionic amphiphilic lipid relative to the total weight of the composition.

18. The composition according to claim 17, wherein the proportion of water-insoluble ionic amphiphilic lipid is from 0.001% to 2% by weight relative to the total weight of the composition.

19. The composition according to claim 17, wherein said water-insoluble ionic amphiphilic lipid is selected from the group consisting of:
   (i) phospholipids,
   (ii) fatty alcohol phosphonic esters,
   (iii) water-insoluble N-acylated derivatives of glutamic acid,
   (iv) sodium cetyl sulphate,
   (v) sodium cocoyl monoglyceride sulphate, and
   (vi) water-insoluble quaternary ammonium derivatives.

20. The composition according to claim 19, wherein said phospholipid is selected from the group consisting of soya lecithin, egg lecithin, hydrogenated lecithin, phosphatidic acid sodium salt and dipalmitoylphosphatidylcholine.

21. The composition according to claim 19, wherein said fatty alcohol phosphoric ester is selected from the group consisting of monocetyl phosphate, dimyristyl phosphate and the sodium and potassium salts thereof.

22. The composition according to claim 19, wherein said water-insoluble N-acylated glutamic acid derivative is selected from the group consisting of monosodium steroyl glutamate and the monosodium cocoyl-($C_{14}$–$C_{20}$) alkoyl glutamate, the $C_{14}$–$C_{20}$ alkoyl radical being derived from hydrogenated tallow.

23. The composition according to claim 19, wherein said water-insoluble quaternary ammonium derivative is selected from the group consisting of behenyltrimethylammonium chloride, dilauryl-dimethylammonium chloride, distearyldimethylammonium chloride, 4,5-dihydro-1-methyl-2-($C_{14}$–$C_{20}$)alkoyl-1-(2-($C_{14}$–$C_{20}$) alkoylaminoethyl) imidazolium methyl sulphate in which the $C_{14}$–$C_{20}$ alkoyl radicals are derived from hydrogenated tallow, dialkylhydroxyethylmethylammonium methyl sulphate in which the alkyl radicals are derived from hydrogenated or nonhydrogenated tallow, and quaternium-82.

24. The composition according to claim 1, wherein said particles have an average size of about 0.05 µm to 1 µm.

25. The composition according to claim 24 wherein said particles have an average size less than or equal to 0.5 µm.

26. The composition according to claim 1 wherein said particles contain at least one hydrophilic active principle.

27. The composition according to claim 1 wherein said particles contain at least one lipophilic active principle.

28. The composition according to claim 1 wherein said particles contain both at least one hydrophilic active principle and at least one lipophilic active principle.

29. The composition according to claim 1 which further contains in the aqueous phase at least one cosmetically or dermatologically acceptable compound selected from the group consisting of a hydrophilic active principle, a preserving agent, a fragrance, a pigment, a dyestuff, a filler and a gelling agent.

30. The composition according to claim 1 which further comprises liposomes.

31. A method of treatment for hydrating the skin, comprising applying to the part of the skin to be treated a sufficient amount of a composition according to claim 1.

* * * * *